(12) United States Patent
Jaspers (10) Patent No.: US 8,992,564 B2
(45) Date of Patent: Mar. 31, 2015

(54) INSTRUMENT FOR MINIMALLY INVASIVE SURGERY (75) Inventor: Joris Emanuel Nicolaas Jaspers, Bodegraven (NL)

(73) Assignee: Academisch Medisch Centrum van de Universiteit van Amsterdam, Amsterdam (NL)

( * ) Notice: Subject to any disclaimer, the term of this patent is extended or adjusted under 35 U.S.C. 154(b) by 0 days.

(21) Appl. No.: 13/278,502

(22) Filed: Oct. 21, 2011

(65) Prior Publication Data

US 2012/0041478 A1 Feb. 16, 2012

Related U.S. Application Data

(60) Division of application No. 10/966,547, filed on Oct. 15, 2004, now abandoned, which is a continuation of application No. PCT/NL03/00165, filed on Mar. 5, 2003.

(30) Foreign Application Priority Data

Apr. 16, 2002 (NL) .................................. 1020396

(51) Int. Cl.
*A61B 17/00* (2006.01)
*A61B 19/00* (2006.01)
*A61B 17/34* (2006.01)

(52) U.S. Cl.
CPC ............ *A61B 19/22* (2013.01); *A61B 2019/265* (2013.01); *A61B 2017/3409* (2013.01)
USPC ................................ 606/205; 606/130; 606/1

(58) Field of Classification Search
CPC ....................................................... A61B 17/28

USPC ............ 606/205–207, 1, 130; 901/14–15, 18, 901/25; 414/1; 74/490.01
See application file for complete search history.

(56) References Cited

U.S. PATENT DOCUMENTS

| | | | |
|---|---|---|---|
| 2,774,488 A | | 12/1956 | Goertz et al. |
| 3,212,651 A | * | 10/1965 | Specht et al. ....................... 414/7 |
| 3,344,936 A | * | 10/1967 | Saunders, Jr. ...................... 414/6 |
| 3,425,569 A | * | 2/1969 | Haaker .............................. 414/8 |
| 3,481,494 A | * | 12/1969 | Walischmiller .................... 414/1 |
| 3,850,307 A | * | 11/1974 | Motoda .......................... 212/237 |
| 4,221,516 A | * | 9/1980 | Haaker et al. ...................... 414/5 |
| 4,329,111 A | * | 5/1982 | Schmid .......................... 414/733 |
| 4,507,043 A | * | 3/1985 | Flatau ............................ 414/719 |
| 4,756,655 A | * | 7/1988 | Jameson ............................ 414/2 |
| 5,052,402 A | * | 10/1991 | Bencini et al. ................. 600/564 |

(Continued)

FOREIGN PATENT DOCUMENTS

| | | |
|---|---|---|
| DE | 102005031494 | 1/2007 |
| WO | WO-9426167 | 11/1994 |

(Continued)

*Primary Examiner* — Katherine Dowe
*Assistant Examiner* — Amy Shipley
(74) *Attorney, Agent, or Firm* — Peacock Myers, P.C.; Jeffrey D. Myers; Justin R. Jackson (57) ABSTRACT

An instrument for minimally invasive surgery suitable for use with a manipulator comprising a tube provided at its first end with a mouthpiece wherein control means for the mouthpiece pass through the tube, and wherein at a second end of the tube opposite to the first end comprising the mouthpiece control organs are provided that are coupled with the control means for the mouthpiece that are passing through the tube.

2 Claims, 6 Drawing Sheets

(56) References Cited

U.S. PATENT DOCUMENTS

| | | | |
|---|---|---|---|
| 5,397,323 A * | 3/1995 | Taylor et al. | 606/130 |
| 5,697,939 A * | 12/1997 | Kubota et al. | 606/130 |
| 5,792,165 A * | 8/1998 | Klieman et al. | 606/170 |
| 5,817,084 A * | 10/1998 | Jensen | 606/1 |
| 5,825,536 A | 10/1998 | Yasunaga et al. | |
| 5,876,325 A | 3/1999 | Mizuno et al. | |
| 5,890,396 A * | 4/1999 | Kaneko et al. | 74/490.01 |
| 6,026,701 A * | 2/2000 | Reboulet | 74/471 XY |
| 6,514,239 B2 * | 2/2003 | Shimmura et al. | 606/1 |
| 6,665,554 B1 | 12/2003 | Charles et al. | |
| 6,702,805 B1 | 3/2004 | Stuart | |
| 6,723,106 B1 | 4/2004 | Charles et al. | |
| 6,936,042 B2 | 8/2005 | Wallace et al. | |
| 7,189,246 B2 * | 3/2007 | Otsuka et al. | 606/130 |
| 7,556,626 B2 * | 7/2009 | Ueda et al. | 606/1 |
| 7,706,000 B2 * | 4/2010 | Cohen et al. | 356/614 |
| 7,841,979 B2 * | 11/2010 | Hirose | 600/102 |
| 7,874,227 B2 * | 1/2011 | Sanchez | 74/490.03 |
| 8,048,088 B2 * | 11/2011 | Green et al. | 606/130 |
| 2001/0027313 A1 * | 10/2001 | Shimmura et al. | 606/1 |
| 2002/0169440 A1 * | 11/2002 | Jensen | 606/1 |
| 2003/0109825 A1 * | 6/2003 | Loser | 604/131 |
| 2004/0138524 A1 * | 7/2004 | Ueda et al. | 600/102 |
| 2004/0172012 A1 * | 9/2004 | Otsuka et al. | 606/1 |
| 2005/0058929 A1 | 3/2005 | Kennedy et al. | |
| 2005/0119641 A1 * | 6/2005 | Jaspers | 606/1 |
| 2009/0030429 A1 * | 1/2009 | Madhani et al. | 606/130 |
| 2010/0121347 A1 * | 5/2010 | Jaspers | 606/130 |
| 2012/0143212 A1 * | 6/2012 | Madhani et al. | 606/130 |
| 2012/0158013 A1 * | 6/2012 | Stefanchik et al. | 606/130 |
| 2012/0158014 A1 * | 6/2012 | Stefanchik et al. | 606/130 |
| 2013/0296882 A1 * | 11/2013 | Kim et al. | 606/130 |
| 2014/0052156 A1 * | 2/2014 | Morley et al. | 606/130 |
| 2014/0107666 A1 * | 4/2014 | Madhani et al. | 606/130 |

FOREIGN PATENT DOCUMENTS

| | | |
|---|---|---|
| WO | WO 96/39944 | 12/1996 |
| WO | WO 99/50721 | 10/1999 |
| WO | WO-0028882 | 5/2000 |
| WO | WO-03086219 | 10/2003 |
| WO | WO-2004037103 | 5/2004 |

* cited by examiner

VIEW A

INSTRUMENT FOR MINIMALLY INVASIVE SURGERY

CROSS-REFERENCE TO RELATED APPLICATIONS

This application is a Divisional application of U.S. Ser. No. 10/966,547 entitled "Manipulator for an Instrument for Minimally Invasive Surgery, and Such an Instrument" filed Oct. 15, 2004, which is a continuation application of International Patent Cooperation Treaty (PCT) Application Serial No. PCT/NL2003/00165, entitled "Manipulator for an Instrument for Minimally Invasive Surgery, and Such an Instrument", to Academisch Medisch Centrum, filed on Mar. 5, 2003, which is a continuation application of Netherlands Patent Application Serial No. NL 1020396, to Academisch Medisch Centrum, filed on Apr. 16, 2002, and the specifications and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention

The invention relates to a manipulator for an instrument for minimally invasive surgery, provided with a first moveable carriage, on which first carriage the instrument can be mounted, wherein the first carriage is positioned on a first arm of a parallelogram construction to provide the instrument with a virtual pivoting point in the plane in which—during use—the instrument intersects the body of a patient. The invention also relates to an instrument to be used with such a manipulator, comprising a tube provided at its first end with a mouthpiece and wherein control means for the mouthpiece pass through the tube.

2. Description of Related Art

A manipulator of the kind mentioned in the preamble is known from the International Patent Application No. WO-00/30557.

In the known manipulator the instrument is motor-driven, Such a manipulator is costly, requires the necessary training for use and has the additional disadvantage that the surgeon using the manipulator feels no force feedback from the resistance the instrument encounters during a surgical operation. In addition, the surgeon often experiences a delay between the movement of his hand and that of the instrument.

It is the object of the invention to provide such a manipulator that is simple, less costly, smaller, lighter and providing the surgeon using the manipulator with an undelayed force feedback, as well as allowing the surgeon to assume a natural posture when operating that matches the positioning of the instrument at that moment.

BRIEF SUMMARY OF THE INVENTION

To this end the manipulator according to the invention is characterized in that the proximal end of the manipulator is provided with a handle for operating the instrument, with the handle being placed on, or forming part of a second arm of the parallelogram construction opposite the first arm, such that a body axis of the handle always extends parallel to the instrument.

DESCRIPTION OF THE INVENTION

The manipulator according to the invention has the advantage that there are no motor drives, and with respect to positioning there is a one-to-one coupling between the handle of the manipulator and the instrument being operated with the aid of the manipulator. This is an inestimable advantage to the surgeon using the manipulator, which especially aids the operational ease and the applicability of the manipulator for surgical uses.

To this end it is further advantageous for the handle to be positioned on a moveable second carriage coupled with the first carriage such that when moving the second carriage, the first carriage carries out a corresponding movement in the longitudinal direction of the instrument.

It is further desirable for the instrument to be detachable from the first carriage. This affords the possibility of easily adapting the instrument to the actions to be carried out during the surgical operation, while the necessary sterilization activities can be limited to this instrument.

In this connection, the manipulator according to the invention may be suitably embodied such that a first carriage is provided with couplers designed to co-operate with control organs of the instruments, which couplers are coupled with the handle via interpositioned pull wires. The application of pull wires is favorable both with respect to limiting the weight of the manipulator that has to be displaced during use, and also to limiting friction and to avoiding possible play.

In a further aspect of the invention the manipulator is characterized in that the instrument is coupled with the handle in order to be able to conduct in unison (not delayed) a rotation about the respective body axes.

As already mentioned above, the invention is also embodied in an instrument that is equipped for use with a manipulator as described above. According to the invention, this instrument is characterized in that at a second end of the tube opposite to the first end comprising the mouthpiece, control organs are provided that are coupled with the control means for the mouthpiece that are passing through the tube.

Advantageously this instrument is embodied such that the control organs are flanges mounted on pull tubes passing through the tube and constituting part of the control means. The use of flanges affords the possibility of a readily detachable coupling between the control organs of the instrument and the couplers of the manipulator, which in turn are operated by means of the handle. The advantage of using pull tubes is that they are also suitable for exerting a pushing force.

The instrument according to the invention is preferably characterized in that the mouthpiece is a jaw-like gripping organ comprising two cooperating jaw portions, wherein each jaw portion is coupled with one of the pull tubes.

An optimization of the adjustment potential of the instrument according to the invention is possible if the gripping organ has two orthogonal directions of rotation, both of which are at right angles in relation to the longitudinal axis of the instrument.

It is further preferred for the jaw portions to be spring-activated so as to force the jaw portions apart to open the gripping organ. By thus providing the necessary opening force for opening the jaw portions of the gripping organ locally, by means of a spring, the diameter of the instrument can be kept to a limit; after all, in order to open the jaw portions there is no need for a separate control organ that would have to pass through the tube of the instrument.

Mounting the manipulator on the operating table allows the manipulator to be used as instrument holder or clamp. The freedom of movement of the manipulator may be designed to include the possibility of locking by means of (for example) break shoes operated by means of (for example) a foot pedal. In this way it is possible to use the manipulator hands-free so as to simultaneously allow other tasks to be performed.

Below the invention will be elucidated in more detail with reference to the drawing of a non-limiting preferred exemplary embodiment of the manipulator and the instrument according to the invention.

BRIEF DESCRIPTION OF THE SEVERAL VIEWS OF THE DRAWINGS

The drawing shows in.

Identical reference numbers in the figures refer to similar parts.

DETAILED DESCRIPTION OF THE INVENTION

Figure 1:
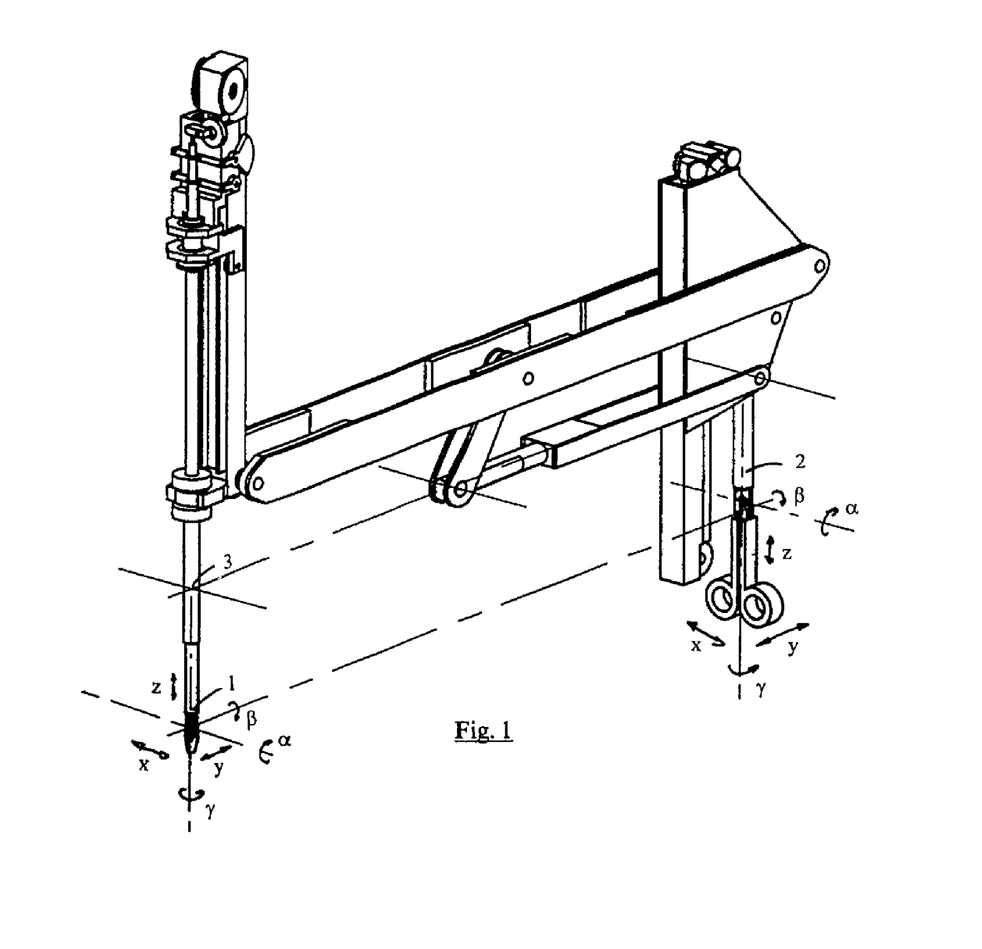
FIGS. 1 and 2 the manipulator with the instrument according to the invention.

Referring to FIG. 1, this figure shows an instrument 1 for laparoscopic surgery, which may be partly within the body of a patient and enjoying six degrees of freedom indicated at the mouthpiece of the instrument, being the three translations x, y and z and the three rotations $\alpha$, $\beta$ arid $\gamma$. All these movements are controlled by operating a handle 2, which enjoys the same degrees of freedom, and which during operation of the handle relays the same one-to-one to the mouthpiece of the instrument. In addition, there is a seventh degree of freedom formed by the open and close movement of the handle 2 and the open and close movement of the jaws of the mouthpiece coupled thereto, as will be explained below.

At the place where via an incision the instrument 1 is inserted in a patient's body, the instrument 1 has, according to the invention, an invariant point 3. When operating the instrument 1 by means of the handle 2, this invariant point 3 forms a virtually fixed point of rotation for the instrument 1.

Figure 2:
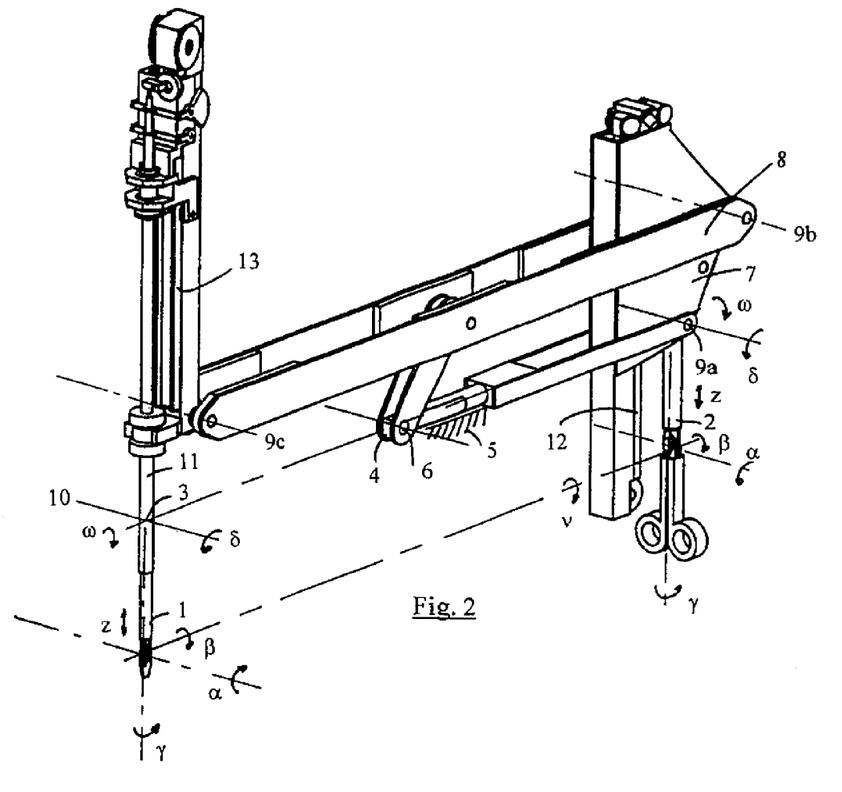

With reference to FIG. 2, it is shown that the basis of the manipulator is formed by a main axis 4 that is capable of carrying out a rotation $\omega$ due to said main axis 4 being accommodated in a bearings 5 coupled with the solid world. This solid world is preferably formed by an operating table. With this main axis 4 a known so-called parallelogram mechanism is connected of which plates 6 and 7 and a tube 8 are elements. By means of this parallelogram mechanism a rotation $\delta$ of the handle 2 about axis 9a is translated into a corresponding rotation $\delta$ about the axes 9b and 9c and axis 10, which is located outside the parallelogram mechanism and (in its extended direction) intersects the main rotation axis 4. This point of intersection coincides with the above-mentioned incision in the patient's body, which coincides with the above referred-to fixed virtual point of rotation. The foregoing thus explains that the instrument 1 is capable of carrying out two rotations $\delta$ and $\omega$ about the fixed virtual point of rotation 3.

For the control of other movements the instrument is capable of, there are, for example, pull-wires leading from the handle 2 through the manipulator to the instrument. The movement of handle 2 and instrument 1 in the longitudinal direction z of the instrument occurs, for example, due to the handle and instrument being situated on carriages 12 and 13 that are moveable along guidings.

The working of the instrument according to the invention will now be further elucidated with reference to the FIGS. 3-6.

Figure 3:
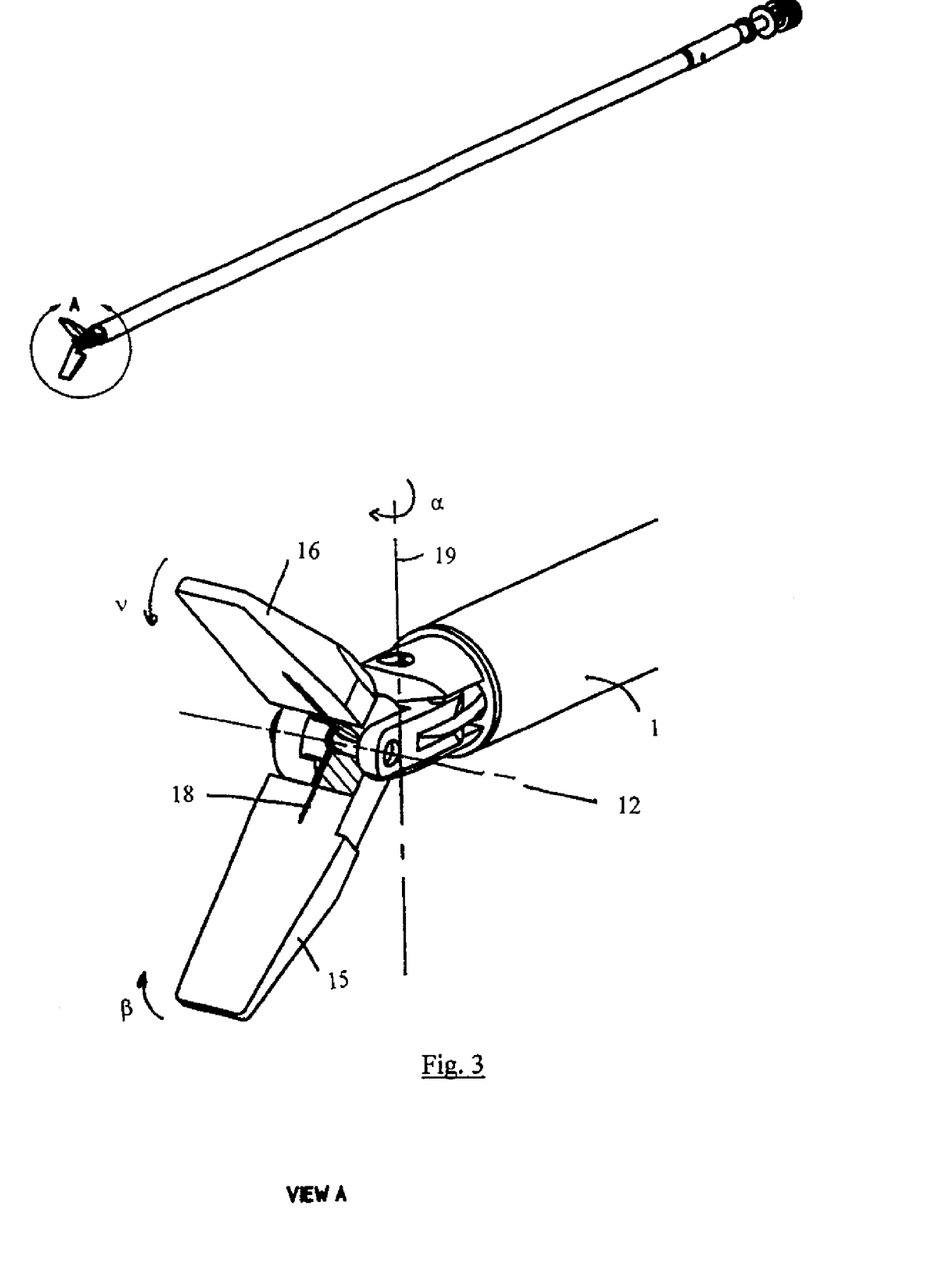
FIG. 3 the whole instrument according to the invention and a detailed view of the mouthpiece.

In FIG. 3 is shown that the mouthpiece of the instrument 1 is embodied as jaw-like gripping organ comprising two cooperating jaw portions 15, 16, each of which is able to rotate individually about axis 17. The rotations $\beta$ and $\nu$ of the jaw portions 15 and 16 are each controlled separately by means of cables that are connected to pull tubes 23 and 22 extending in the instrument 1 (see also FIG. 4). By contracting the pull tubes 23 and 22 simultaneously the jaw portions 15 and 16 are caused to close. The jaw portions are also spring-activated by means of a spring 18 (see FIG. 3), which produces an opening force for the jaw portions 15, 16.

Figure 5:
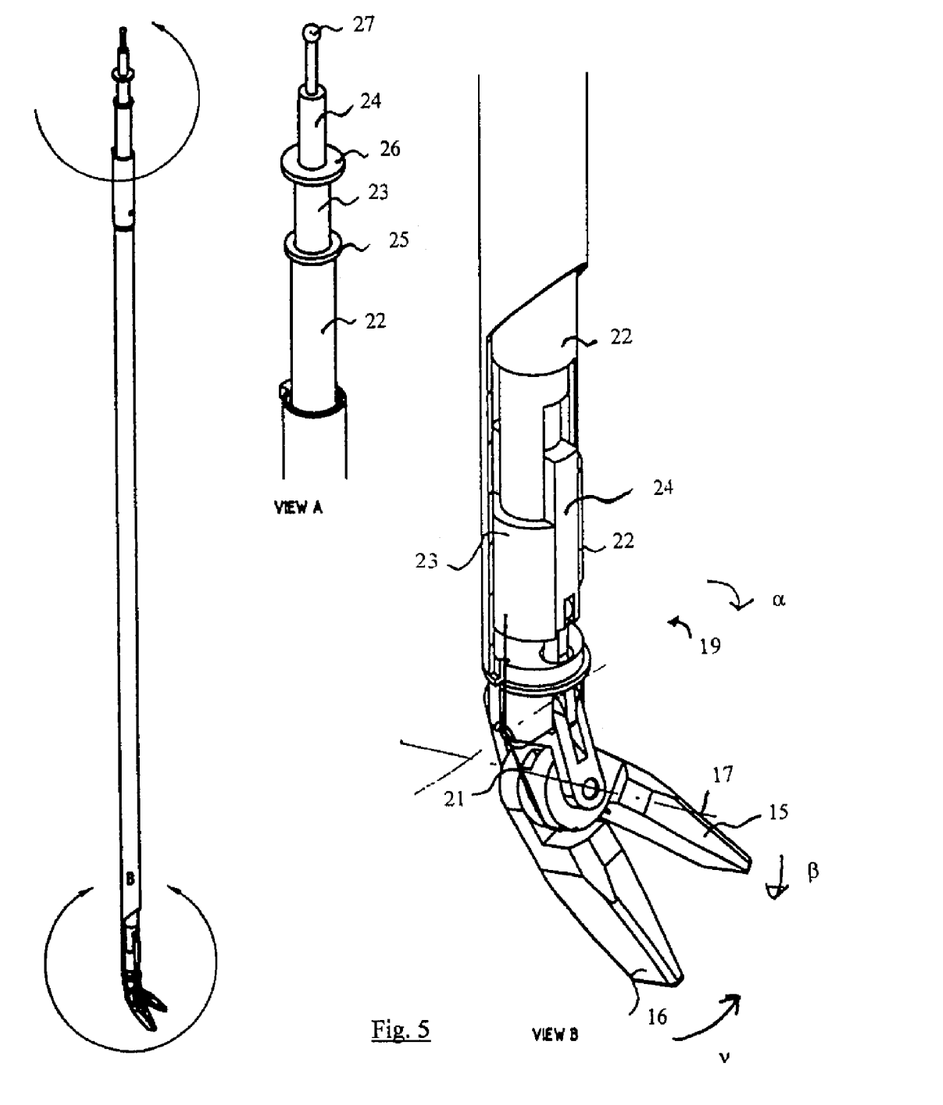
FIG. 5 the instrument according to the invention as shown in FIG. 4, with the mouthpiece being slightly rotated.

FIG. 5 shows that when only pull tube 22 is contracted and pull tube 23 is slack, both jaw portions 15, 16 of jaw-like gripping organ 21 will rotate about axis 17 in direction $\nu$. The instrument 1 is further embodied such that the jaw portions 15, 16 are also able to rotate about an axis 19. To this end a pull-push tube is used which, when pushing in the direction of the jaw portions 15, 16, will rotate the same in the direction of rotation indicated by $\alpha$.

Figure 4:
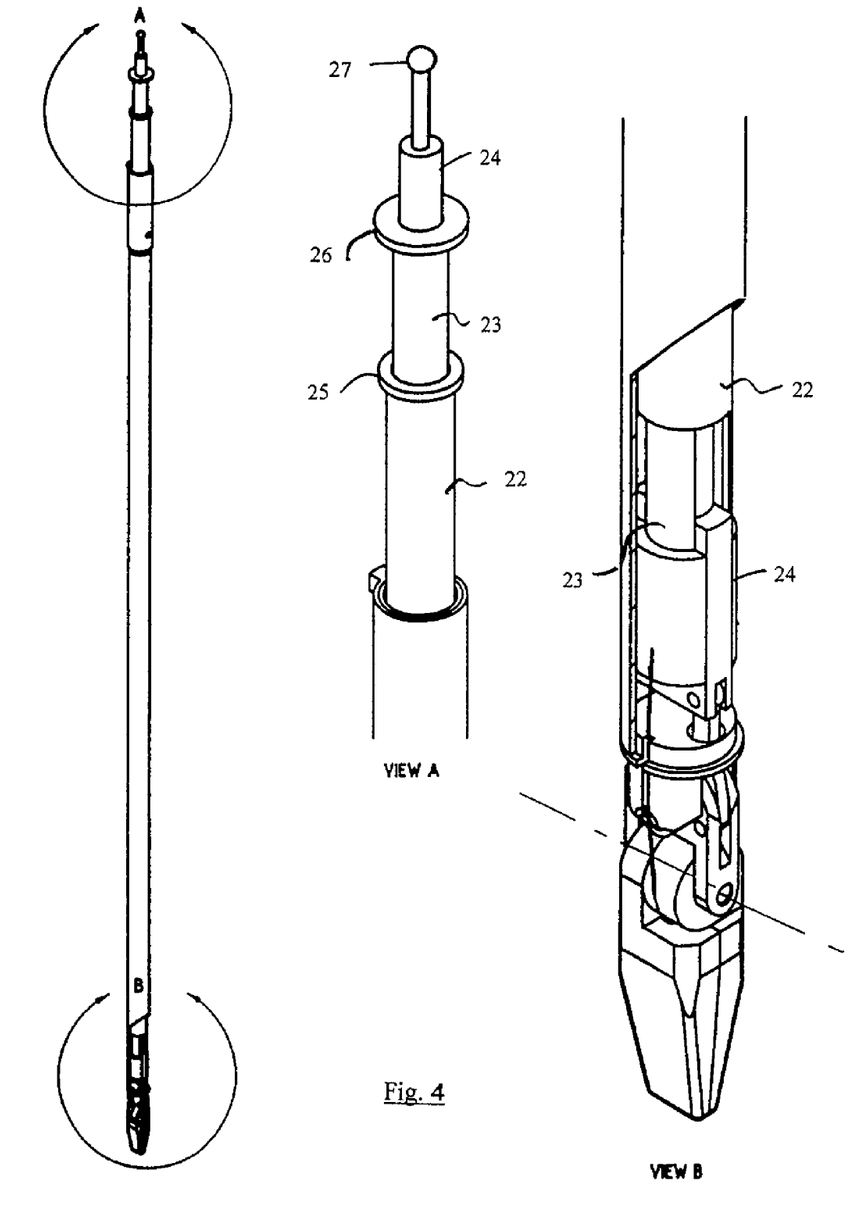
FIG. 4 the whole instrument according to the invention, as well as a detailed view of a first end and a detailed view of a second end.

FIGS. 4 and 5 further show that at the end furthest from the jaw portions 15, 16, the pull tubes 22 and 23 are provided with flanges 25 and 26. At the respective end, pull-push rod 24 is provided with a ball 27. The function of the flanges 25 and 26 and the ball 27 will become clear in the explanation below referring to FIG. 6.

Figure 6:
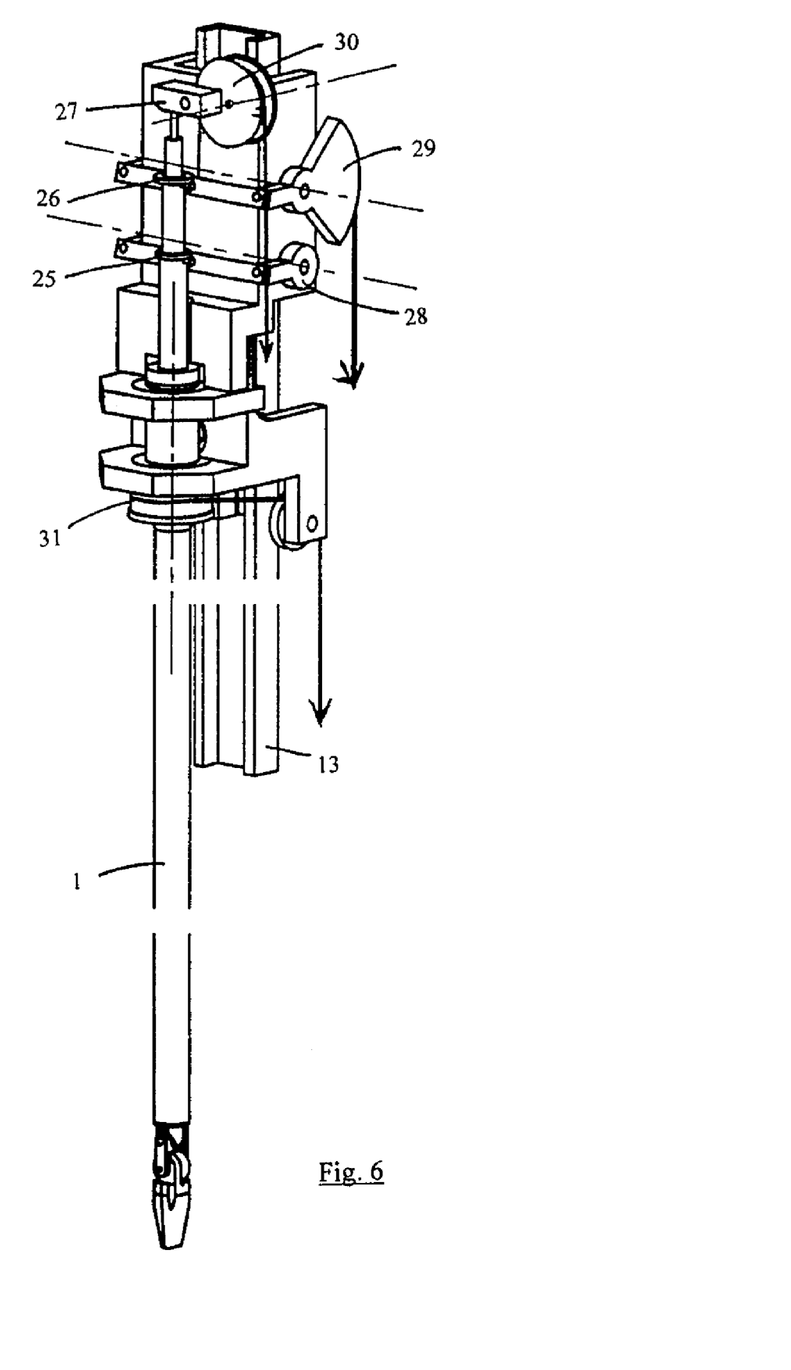
FIG. 6 the instrument according to the invention in mounted position together with a portion of the manipulator.

FIG. 6 shows the instrument 1 mounted on the carriage 13 and moveable along a guiding. The flanges 25 and 26 that are coupled via the above-mentioned pull rods with the jaw portions 15, 16 of the mouthpiece, are operated by means of levers 28 and 29, which are part of the manipulator. The pull-push rod 24 is operated by a disc 30 connected to the ball 27. This latter connection is designed such that thanks to the shape of the ball 27, the instrument 1 is rotatable about its longitudinal axis. By controlling the levers 28 and 29 and the disc 30, the rotations $\alpha$, $\beta$ and $\nu$ of the jaw portions 15, 16 are controlled. Incidentally, the ball 27 and the disc 30 cooperating therewith, as also other construction parts, may be replaced by another construction working in a similar manner, for example, by a rotatable flange controlled by means of a moveable carriage. Rotation $\gamma$ of the instrument 1 is effected by operating the disc 31.

The coupling of the levers 28 and 29 and disc 30 with the handle 2, is in the present exemplary embodiment effected by means of pull wires. However, within the scope of the invention it is also possible to provide other types of couplings between the handle 2 and the operating members of the instrument 1. Such couplings may be bowden cables, hydraulics, chains, bands or the like. All this lies within the scope of the person skilled in the art and requires no further explanation.

What is claimed is:

1. An instrument and a manipulator for minimally invasive surgery, wherein the manipulator has a main axis accommodated in a bearing for coupling the manipulator to a solid world, and provided with a first moveable carriage on which the instrument is mounted, wherein said first movable carriage is positioned on a first arm that connects on a first side of a parallelogram construction of the manipulator to said a parallelogram construction which is provided with a main axis that is accommodated in a bearing, and a handle being placed on, or forming part of, a second arm that connects on a second side opposite to the first side of said parallelogram construction of said manipulator to said parallelogram construction wherein both the instrument in its mounted position and the handle extend below said main axis, wherein a body axis of said handle always extends parallel to the instrument, and wherein the instrument is coupled with the handle in order to conduct a rotation of the instrument about its respective body axes in unison with the handle, wherein the instrument comprises a tube provided at its first end with a mouthpiece wherein pull tubes and a pull-push rod that pass through the tube are provided for controlling the mouthpiece, and wherein flanges and a ball are provided at a second end of the tube opposite to the first end comprising the mouthpiece, which flanges are mounted on said pull tubes, and which ball is provided on the pull-push rod so that jaw portions are rotatable in three directions, including rotation of the instrument about its longitudinal axis, by operation of the flanges and the ball by and in accordance with movement of said handle, wherein the mouthpiece is a jaw-like gripping organ comprising two cooperating jaw portions, wherein each jaw portion is coupled with one of the pull tubes, wherein the jaw portions are spring activated so as to force the jaw portions apart to open the gripping organ.

2. An instrument according to claim 1, wherein the gripping organ has two orthogonal directions of rortation, both of which are at right angles in relation to the longitudinal axis of the instrument.

\* \* \* \* \*